United States Patent
Mason

(10) Patent No.: US 12,190,414 B2
(45) Date of Patent: *Jan. 7, 2025

(54) ITERATIVE IMAGE RECONSTRUCTION

(71) Applicant: Elekta Limited, Crawley (GB)

(72) Inventor: Jonathan Hugh Mason, Edinburgh (GB)

(73) Assignee: Elekta Limited, Crawley (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/406,835

(22) Filed: Jan. 8, 2024

(65) Prior Publication Data
US 2024/0303878 A1   Sep. 12, 2024

Related U.S. Application Data

(63) Continuation of application No. 17/303,009, filed on May 18, 2021.

(51) Int. Cl.
| | |
|---|---|
| *G06T 11/00* | (2006.01) |
| *G06N 5/04* | (2023.01) |
| *G06N 20/00* | (2019.01) |
| *A61N 5/10* | (2006.01) |

(52) U.S. Cl.
CPC .............. *G06T 11/005* (2013.01); *G06N 5/04* (2013.01); *G06N 20/00* (2019.01); *A61N 5/1039* (2013.01); *G06T 2211/424* (2013.01)

(58) Field of Classification Search
None
See application file for complete search history.

(56) References Cited

U.S. PATENT DOCUMENTS

| | | | |
|---|---|---|---|
| 8,977,026 B2 * | 3/2015 | Bar-Shalev | G06T 7/74 250/363.04 |
| 9,489,752 B2 | 11/2016 | Kim et al. | |
| 11,915,346 B2 * | 2/2024 | Mason | G06T 11/005 |
| 2018/0229056 A1 | 8/2018 | Paysan et al. | |
| 2022/0375140 A1 | 11/2022 | Mason | |
| 2023/0264045 A1 * | 8/2023 | Sjolund | A61N 5/1031 600/1 |

(Continued)

FOREIGN PATENT DOCUMENTS

| | | |
|---|---|---|
| CN | 117957574 | 4/2024 |
| WO | 2022243391 | 11/2022 |

OTHER PUBLICATIONS

U.S. Appl. No. 17/303,009 U.S. Pat. No. 11,915,346, filed May 18, 2021, Iterative Image Reconstruction.

(Continued)

*Primary Examiner* — Dov Popovici
(74) *Attorney, Agent, or Firm* — Schwegman Lundberg & Woessner, P.A.

(57) ABSTRACT

Systems and methods are provided for performing operations including: accessing a current structural estimate of a region of interest; generating a first simulated X-ray measurement based on the current structural estimate of the region of interest; receiving a first real X-ray measurement; and generating an update to the current structural estimate of the region of interest as a function of the first simulated X-ray measurement and the first real X-ray measurement, the update being generated invariant on the current structural estimate.

20 Claims, 12 Drawing Sheets

(56) References Cited

U.S. PATENT DOCUMENTS

2023/0285776 A1* 9/2023 Lachaine .............. A61N 5/1049

OTHER PUBLICATIONS

"U.S. Appl. No. 17/303,009, Notice of Allowance mailed Oct. 25, 2023", 13 pages.

"U.S. Appl. No. 17/303,009, Corrected Notice of Allowability mailed Nov. 6, 2023", 2 pgs.

"International Application Serial No. PCT EP2022 063485, International Preliminary Report on Patentability mailed Nov. 30, 2023", 8 pgs.

"International Application Serial No. PCT EP2022 063485, International Search Report mailed Sep. 14, 2022", 3 pgs.

"International Application Serial No. PCT EP2022 063485, Written Opinion mailed Sep. 14, 2022", 6 pgs.

Erdogan, Hakan, "Ordered subsets algorithms for transmission tomography", Physics in Medicine and Biology 44.11, (1999), 19 pgs.

Kim, Donghwan, "Combining ordered subsets and momentum for accelerated X-ray CT image reconstruction", IEEE transactions on medical imaging 34.1, (2014), 167-178.

Kim, Donghwan, "Accelerating Xray CT ordered subsets image reconstruction with Nesterovs first order methods", Proc. Intl. Mtg. on Fully 3D Image Recon. in Rad. and Nuc. Med., (2013), pp. 22-25.

Mason, Jonathan H., "Quantitative cone-beam CT reconstruction with polyenergetic scatter model fusion", Physics in Medicine and Biology 63.22, (Jan. 2020), 28 pgs.

Mason, Jonathan H., "Polyquant CT: direct electron and mass density reconstruction from a single polyenergetic source", Physics in Medicine and Biology 62.22, (2019), 23 pgs.

Wang, Adam S., "Accelerated statistical reconstruction for C-arm cone-beam CT using Nesterov's method", Medical physics 42.5, (2015), 2699-2708.

* cited by examiner

ITERATIVE IMAGE RECONSTRUCTION

CLAIM FOR PRIORITY

This application is a continuation of and claims the benefit of priority of U.S. application Ser. No. 17/303,009, filed May 18, 2021, which is hereby incorporated by reference in its entirety.

TECHNICAL FIELD

Embodiments of the present disclosure pertain generally to iterative image reconstruction.

BACKGROUND

Radiation therapy (or "radiotherapy") can be used to treat cancers or other ailments in mammalian (e.g., human and animal) tissue. One such radiotherapy technique involves irradiation with a Gamma Knife, whereby a patient is irradiated by a large number of low-intensity gamma ray beams that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator (MLC)). The intensity and shape of the radiation beam can be adjusted by collimation to avoid damaging healthy tissue (e.g., OARs) adjacent to the targeted tissue by conforming the projected beam to a profile of the targeted tissue.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task can be a time-consuming trial-and-error process that is complicated by the various OARs because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, computed tomography (CT), nuclear magnetic resonance (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider can delineate the target tumor that is to receive a prescribed radiation dose using a manual technique, and the health care provider can similarly delineate nearby tissue, such as organs, at risk of damage from the radiation treatment. Alternatively, or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

The treatment plan can then be later executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linear accelerator—"linac") is very important in order to ensure the target tumor and not healthy tissue is irradiated.

Since most patients receive more than one fraction of radiation as part of a course of therapy, and because the anatomy may change (deform) between these fractions, it is not straightforward to sum the doses delivered during the individual fractions so the physician can accurately gauge how the treatment is proceeding relative to the original intent as defined by the prescription.

Overview

In some embodiments, a system is provided that includes: a memory; and one or more processors that, when executing instructions stored in the memory, are configured to perform operations comprising: accessing a current structural estimate of a region of interest; generating a first simulated X-ray measurement based on the current structural estimate of the region of interest; receiving a first real X-ray measurement; and generating an update to the current structural estimate of the region of interest as a function of the first simulated X-ray measurement and the first real X-ray measurement, the update being generated invariant on the current structural estimate.

In some implementations, the first real X-ray measurement is received from a cone-beam computed tomography (CBCT) system or computed tomography (CT) system, and wherein the operations further comprise computing the update as a derivative of a statistical objective function with respect to the first simulated X-ray measurement.

In some implementations, the operations further comprise: linearly projecting the update to the current structural estimate into an image space to form a perturbation; scaling the perturbation by a scalar for stability; and subtracting the scaled perturbation from the current structural estimate to generate an updated structural estimate.

In some implementations, the operations further comprise: applying at least one of regularization, momentum or denoising to the updated structural estimate.

In some implementations, the current structural estimate comprises an X-ray attenuation map that represents a three-dimensional (3D) model of the region of interest.

In some implementations, the X-ray attenuation map comprises a linear X-ray attenuation map.

In some implementations, generating the first simulated X-ray measurement based on the current structural estimate of the region of interest comprises applying the current structural estimate to a model that generates an expected output of a real X-ray measurement.

In some implementations, the current structural estimate comprises an X-ray attenuation map, and wherein the model generates the expected output of the real X-ray measurement, for a given measurement index i per number of detector elements in a cone-beam computed tomography (CBCT) system, in accordance with: $z_i = b_i * \exp(-[Ax]_i) + r_i$, where b is an incident intensity of flood field, A is a system projection matrix describing a combination of each image pixel at each detector element, x is the current X-ray attenuation map, exp is an exponential function, and r is background noise including scatter.

In some implementations, the operations further comprise re-estimating r representing the background noise including scatter based on the current structural estimate at each iteration of generating the update.

In some implementations, the model comprises a modeling function representing beam hardening from a polyenergetic source, the modeling function comprising a machine learning technique that is trained to establish a relationship between a training real X-ray measurement and a training known simulated X-ray measurement; a linear model; or a non-linear model that fits X-ray data to some nominal value comprising at least one of relative electron density, mass density, monoenergetic attenuation, proton stopping power, or bone mineral density.

In some implementations, the operations further comprise repeating the generating of a simulated X-ray measurement, receiving of a real X-ray measurement, and generating of an update to the current structural estimate for multiple sets of simulated and real X-ray measurements.

In some implementations, the operations further comprise: accessing an updated structural estimate of the region of interest; generating a second simulated X-ray measurement based on the updated structural estimate of the region of interest; receiving a second real X-ray measurement; and generating a further update to the updated structural estimate of the region of interest as a function of the second simulated X-ray measurement and the second real X-ray measurement.

In some implementations, the operations further comprise: accessing an objective function comprising a negative log-likelihood (NLL) function; computing a loss by applying the NLL function to a combination of the first simulated X-ray measurement and the first real X-ray measurement; and in response to determining that the loss fails to satisfy a criterion, performing the update to the current structural estimate, the criterion comprising a difference between adjacent updates falling below a threshold, a number of iterations falling below a maximum iteration value, an elapsed time falling below a maximum time limit, or input requesting termination and display of a result.

In some implementations, the current structural estimate comprises an X-ray attenuation map, and wherein the update to the current structural estimate of the region of interest is computed in accordance with: $A^T(y/(b*\exp(-Ax)+r)-1)$, where A is a system projection matrix describing a combination of each image pixel at each detector element, $A^T$ is a transpose of the system projection matrix, y is the first real X-ray measurement, b is an incident intensity of flood field, x is the current X-ray attenuation map, exp is an exponential function, and r is background noise including scatter.

In some implementations, the operations further comprise: receiving a plurality of real X-ray measurements; partitioning the plurality of real X-ray measurements into measurement groups, a first measurement group of the measurement groups corresponding to a group of X-ray measurements used to update the current structural estimate, and a second measurement group of the measurement groups corresponding to a group of X-ray measurements that is skipped from updating the current structural estimate; determining that the first real-X-ray measurement falls within the first measurement group; and in response to determining that the first real-X-ray measurement falls within the first measurement group, performing the update to the current structural estimate.

In some implementations, the operations further comprise: collecting a plurality of updates to the structural estimate, each of the plurality of updates being associated with a respective iteration; identifying a pattern of updates based on the collected plurality of updates; and performing the update to the current structural estimate based on the identified pattern of updates.

In some embodiments, a method is provided for accessing a current structural estimate of a region of interest; generating a first simulated X-ray measurement based on the current structural estimate of the region of interest; receiving a first real X-ray measurement; and generating an update to the current structural estimate of the region of interest as a function of the first simulated X-ray measurement and the first real X-ray measurement, the update being generated invariant on the current structural estimate.

In some implementations, the method includes computing the update as a derivative of a statistical objective function with respect to the first simulated X-ray measurement.

In some implementations, the method includes linearly projecting the update to the current structural estimate into an image space to form a perturbation; scaling the perturbation by a scalar for stability; and subtracting the scaled perturbation from the current structural estimate to generate an updated structural estimate.

In some implementations, the method includes applying at least one of regularization, momentum or denoising to the updated structural estimate.

In some implementations, the current structural estimate comprises an X-ray attenuation map that represents a three-dimensional (3D) model of the region of interest.

In some implementations, the X-ray attenuation map comprises a linear X-ray attenuation map.

In some implementations, generating the first simulated X-ray measurement based on the current structural estimate of the region of interest comprises applying the current structural estimate to a model that generates an expected output of a real X-ray measurement.

In some embodiments, a non-transitory computer-readable medium is provided that includes non-transitory computer-readable instructions that, when executed by one or more processors, configure the one or more processors to perform operations comprising: accessing a current structural estimate of a region of interest; generating a first simulated X-ray measurement based on the current structural estimate of the region of interest; receiving a first real X-ray measurement; and generating an update to the current structural estimate of the region of interest as a function of the first simulated X-ray measurement and the first real X-ray measurement, the update being generated invariant on the current structural estimate.

In some implementations, the operations further comprise: computing the update as a derivative of a statistical objective function with respect to the first simulated X-ray measurement.

In some implementations, the operations further comprise: linearly projecting the update to the current structural estimate into an image space to form a perturbation; scaling the perturbation by a scalar for stability; and subtracting the scaled perturbation from the current structural estimate to generate an updated structural estimate.

In some implementations, the operations further comprise: applying at least one of regularization, momentum or denoising to the updated structural estimate.

In some implementations, the current structural estimate comprises an X-ray attenuation map that represents a three-dimensional (3D) model of the region of interest.

In some implementations, the X-ray attenuation map comprises a linear X-ray attenuation map.

In some implementations, generating the first simulated X-ray measurement based on the current structural estimate of the region of interest comprises applying the current structural estimate to a model that generates an expected output of a real X-ray measurement.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
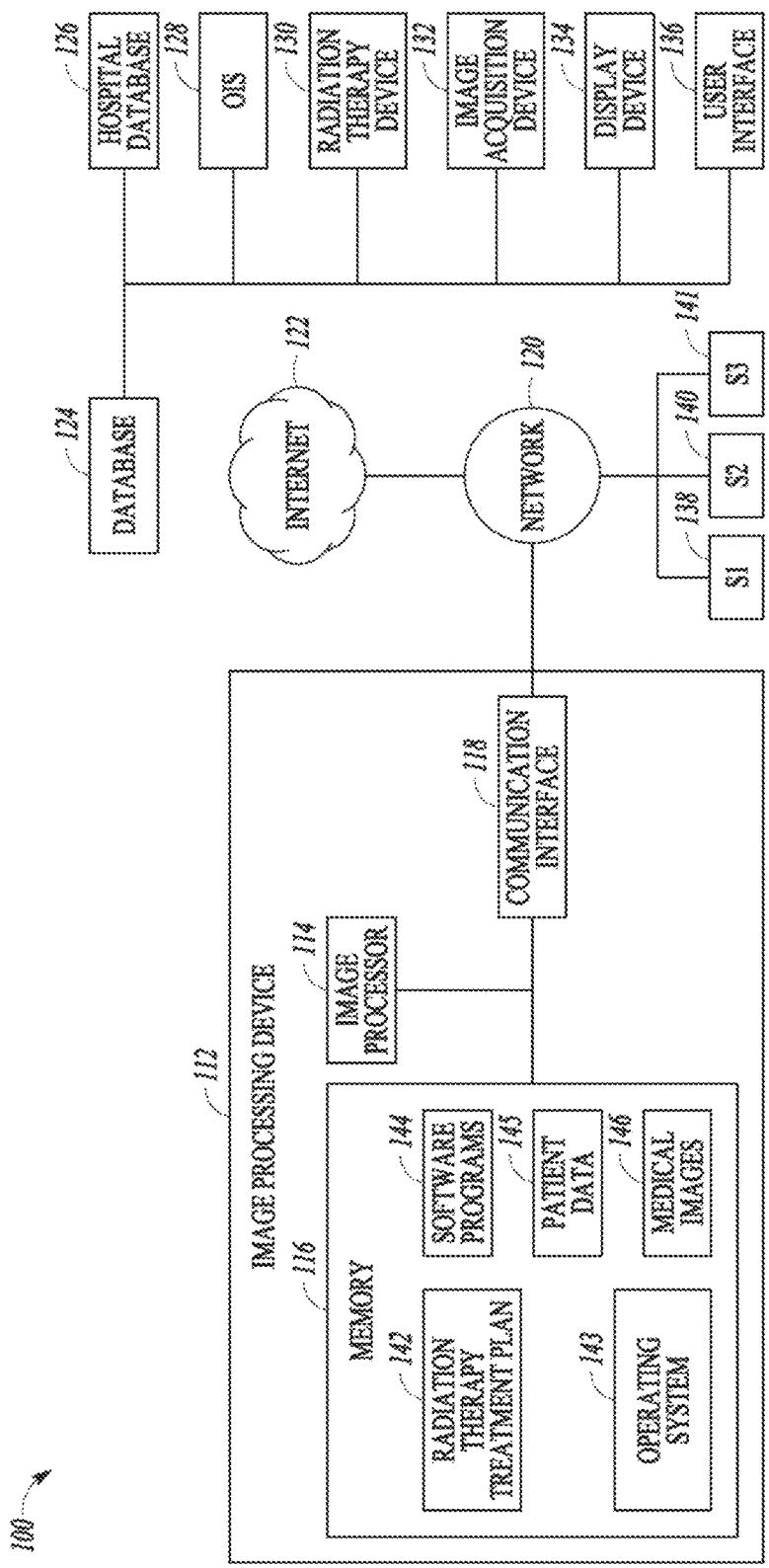
FIG. 1 illustrates an example radiotherapy system, according to some embodiments of the present disclosure.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized, and that structural, logical and electrical changes may be made without departing from the scope of the present disclosure. The following detailed description is, therefore, not be taken in a limiting sense, and the scope of the present disclosure is defined by the appended claims and their equivalents.

Physically quantifying reconstructions from CT is highly valuable in some medical practices. In radiation therapy for example, the electron density inferred from CT images of the patient allows the dose deposition from the treatment beam to be accurately modelled. Additionally, quantifying the bone mineral density allows osteoporosis to be characterized and the risk of bone fractures to be assessed. Due to the non-linear energy-dependence of X-ray attenuation, however, mapping from a set of raw measurements to a consistent physically quantitative reconstruction (e.g., a structural estimate) is not straightforward, and requires both actively accounting for the polyenergetic effects such as beam hardening and establishing a relation to the quantity of interest.

Mapping from CT to physical density is usually treated in a several step process: linearizing the measurements by correcting for scatter, taking the logarithm and non-linearly calibrating from a polyenergetic to approximate monoenergetic source; inverting the linearized projections with analytic or iterative reconstruction algorithms; then finally applying a non-linear calibration to mass or electron density. One approach to mapping from a single polyenergetic to a monoenergetic measurement is to model the X-ray attenuation explicitly in terms of physical processes, given quantitative physical parameters of interest. One such choice is to model the photoelectric and Compton effects in terms of relative atomic number and electron density, which is reasonably accurate for relevant elements and energies. Given measurements from two sufficiently different spectra-a technique known as dual-energy CT (DECT)—a projection of Compton attenuation can be uniquely determined, of which electron density is an analytic function. This DECT technique effectively bypasses the need for assumptions such as water-bone compositions, so can be applicable to a wider range in materials.

X-ray scatter is a large source of errors in CT, where scattered X-rays corrupt the line of sight attenuation models used during image reconstruction (e.g., generation of the structural estimate). In CBCT, due to its large field of view, the magnitude of these interfering X-rays is commonly of the same order of magnitude as the signal of interest and can even be considerably higher. With this, artifacts and inaccuracies in the reconstruction are inevitable unless it can be correctly compensated. A fundamental reason why estimating scatter is difficult is that unlike modelling attenuation, requiring a single path from source to detector for each measurement, one may need to consider every possible path a photon can take through various numbers of scattering events to get the full picture to generate the structural estimate. This can therefore not only be dependent on the attenuating materials and intensity along a single pencil beam, but it can be dependent on the full projection fluence and the complete structure of the specimen. Not only is calculating all these paths computationally exhaustive, but one does not even have knowledge of the structure of the specimen prior to reconstruction, since this is the task of the reconstruction itself. This therefore presents a dependency problem, where one may need the image to estimate scatter, but cannot form the image accurately because of scatter contamination.

Some existing approaches calculate the perturbation (changes/updates) to the structural estimate at each iteration as the gradient of a statistical objective function with respect to the structural estimate itself, which is also computationally exhaustive and still leads to inaccuracies in the structural estimate. Namely, existing approaches provide iterative reconstruction methods that minimize an objective function at each iteration, which is composed of data consistency and structural penalty terms. These approaches, though, suffer from a large computational expense of each iteration, especially with high-resolution multi-dimensional data; poor convergence rate requiring many iterations; unstable and divergent behavior due to numerical approximations or non-convexity; and the introduction of phantom artefacts from an inaccurate noise model, geometrical errors, inaccurate modelling of the physics, or numerical errors.

The disclosed embodiments address these challenges by updating a structural estimate of a CBCT system (e.g., a real X-ray measurement) based on simulated measurements of the CBCT system which are invariant to (independent of) the structural estimate itself. This yields to increased stability and a faster convergence rate and results in a higher quality image in fewer iterations. In this way, the overall efficiency of the computing device is improved, as less resources are consumed in generating a structural estimate of a CBCT system with greater accuracy than traditional approaches. Specifically, CBCT images may be generated using a kV imaging detector affixed to a linear accelerator. These images can be used to generate 3D images for image guidance and online adaptive radiotherapy prior to each radiation treatment. Although very useful, these images have suffered from lower image quality than diagnostic CT in previous approaches. Iterative image reconstruction can be used to improve the CBCT images and the disclosed techniques improve both image quality and reconstruction time for generating such CBCT images over typical systems.

Specifically, according to some examples, a current structural estimate (e.g., an X-ray attenuation map) of a region of interest is accessed. The disclosed techniques generate a first simulated X-ray measurement based on the current structural estimate of the region of interest and receive a first real X-ray measurement from a CBCT system or CT system. The disclosed techniques generate an update to the current structural estimate of the region of interest as a function of the first simulated X-ray measurement and the first real X-ray measurement, in which the update is generated invariant on the current structural estimate. This results in faster image reconstruction time for the structure estimate, which also has greater accuracy (e.g., undesirable phantom artefacts, including streaking and shading in the image, are reduced).

FIG. 1 illustrates an example radiotherapy system 100 for providing radiation therapy to a patient. The radiotherapy system 100 includes an image processing device 112. The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 to be used by the radiation therapy device 130.

The image processing device 112 may include a memory device 116, an image processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the image processor 114.

In one embodiment, the software programs 144 may convert medical images of one format (e.g., MRI) to another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo CT image); alternatively, the trained predictive model may convert a CT image into an MRI image. In another embodiment, the software programs 144 may register the patient image (e.g., a CT image or an MR image) with that patient's dose distribution (also represented as an image) so that corresponding image voxels and dose voxels are associated appropriately by the network. In yet another embodiment, the software programs 144 may substitute functions of the patient images or processed versions of the images that emphasize some aspect of the image information. Such functions might emphasize edges or differences in voxel textures, or any other structural aspect useful to neural network learning. In another embodiment, the software programs 144 may substitute functions of the dose distribution that emphasize some aspect of the dose information. Such functions might emphasize steep gradients around the target or any other structural aspect useful to neural network learning. The memory device 116 may store data, including medical images 146, patient data 145, and other data required to create and implement a radiation therapy treatment plan 142.

In yet another embodiment, the software programs 144 may generate a structural estimate (e.g., a 3D model of the region of interest) using an iterative image reconstruction process. The structural estimate may be or include an X-ray attenuation map that represents a 3D model of a region of interest. The structural estimate may be used to estimate or simulate X-ray measurements to be compared with real X-ray measurements for updating the structural estimate. Specifically, the software programs 144 can access a current structural estimate of the region of interest and generate a first simulated X-ray measurement based on the current structural estimate of the region of interest. A simulated X-ray measurement, as referred to herein, represents the expected output of an X-ray detector element when an X-ray source projects one or more X-ray beams through the region of interest towards the X-ray detector element. The simulated X-ray measurement can provide an expected image output that is to be received from the X-ray detector element. The software programs 144 can receive a first real X-ray measurement from a CBCT system (or other CT imaging system, such as an enclosed gantry helical multi-slice CT with a curved detector or tomotherapy system) and generate an update to the current structural estimate of the region of interest as a function of the first simulated X-ray measurement and the first real X-ray measurement. A real X-ray measurement, as referred to herein, is an actual output that is received from a CBCT system (or other CT imaging system, such as an enclosed gantry helical multi-slice CT with a curved detector or tomotherapy system) that represents the amount of X-rays received by and detected by the X-ray detector along different directions, such as in an image form. The update can be generated invariant on (independent of) the current structural estimate. The structural estimate can be used to control one or more radiotherapy treatment parameters by recalculating dose, adjusting one or more radiotherapy treatment machine parameters, or generating a display of the structural estimate on a graphical user interface.

In some embodiments, the software programs 144 generate the first simulated X-ray measurement based on the current structural estimate of the region of interest by applying the current structural estimate to a model that generates an expected output of a real X-ray measurement. In some implementations, the model that generates an expected output of a real X-ray measurement includes a modeling function representing beam hardening from a polyenergetic source. In some implementations, the modeling function that generates an expected output of a real X-ray measurement includes a machine learning technique that is trained to establish a relationship between a training real X-ray measurement and a training known simulated X-ray measurement. In some implementations, the modeling function that generates an expected output of a real X-ray measurement includes a linear model or a non-linear model that fits X-ray data to some nominal value comprising at least one of relative electron density, mass density, monoenergetic attenuation, proton stopping power, or bone mineral density.

As an example, the model generates the expected output of the real X-ray measurement, for a given measurement index i per number of X-ray detector elements in the CBCT system, in accordance with Equation 1:

$$z_i = b_i * \exp(-[Ax]_i) + r_i, \quad (1)$$

where b is an incident intensity of flood field, A is a system projection matrix describing a combination of each image pixel at each detector element, x is the current X-ray attenuation map, exp is an exponential function, and r is background noise including scatter. For example, the model applies the current structural estimate to Equation 1 as x to output the first simulated measurement z. The first simulated measurement can be generated for each of a plurality of X-ray detector elements that are in the CBCT system.

In an example, the value for r representing the noise including scatter can be re-estimated based on the current structural estimate at each iteration. For example, the noise including scatter for a given iteration can be applied to another machine learning technique or model including x (e.g., the current structural estimate) to generate an update and re-estimate the value of the noise including scatter.

In some embodiments, the software programs 144 compute the update to the current structural estimate as a derivative of a statistical objective function with respect to the first simulated X-ray measurement. For example, the statistical objective function can be computed according to Equation 2:

$$A^T(y./b. * \exp(-Ax) + r) - 1) \quad (2)$$

where A is a system projection matrix describing a combination of each image pixel at each detector element, A is a transpose of the system projection matrix, y is the first real X-ray measurement, b is an incident intensity of flood field, x is the current X-ray attenuation map, exp is an exponential function, and r is background noise including scatter. The update to the current structural estimate represents a perturbation to the current structural estimate. Namely, the update is linearly projected to the current structural estimate into an image space to form a perturbation. The perturbation is scaled by a scalar for stability and the scaled perturbation is subtracted from the current structural estimate to generate an updated structural estimate.

In some implementations, after the structural estimate is updated, at least one of regularization, momentum or denoising is applied to the updated structural estimate to improve the image quality of the 3D model represented by the structural estimate.

In some embodiments, the computation of the update and the updating of the structural estimate is conditioned on and performed in response to a computation of a negative log-likelihood (NLL) function (e.g., a loss function). Specifically, the loss function is computed as a combination of the first simulated X-ray measurement and the first real X-ray measurement, such as in accordance with Equation 3:

$$NLL = sum(z_i - y_i * \log(z_i)) \quad (3)$$

which may represent a sum of the differences between each of the plurality of simulated and real measurements of the X-ray CBCT system. Namely, a plurality of simulated measurements each associated with a different X-ray detector can be generated in accordance with Equation 1. The corresponding real X-ray measurements can be received from the X-ray detector, such as from the image acquisition device 132. The differences between each simulated measurement and the corresponding real measurement can be computed and summed. If the sum of these differences is below a threshold (e.g., satisfies a stopping criterion), then the update to the structural estimate is not performed. On the other hand, in response to determining that the loss fails to satisfy the stopping criterion (e.g., if the sum of these differences is above the threshold), the update to the current structural estimate is performed.

In some cases, instead of or in addition to conditioning the performance of the update on the sum of the differences or the loss function defined by Equation 3, the stopping criterion (e.g., the condition for not performing the update) can include a difference between adjacent updates falling below a threshold. For example, the software programs 144 can access a previous update value(s) and can generate a new update value based on the currently generated simulated X-ray measurement. The software programs 144 can compute a difference between these two adjacent or subsequent update values to the structural estimate. The software programs 144 can compare this difference to a stopping threshold and if the difference is below the stopping threshold, the software programs 144 may avoid performing the update to the structural estimate. If the difference is above the stopping threshold, the software programs 144 can perform the update to the structural estimate, such as in accordance with Equation 2.

In some cases, instead of or in addition to conditioning the performance of the update on the sum of the differences or the loss function defined by Equation 3, the stopping criterion (e.g., the condition for not performing the update) can include a number of iterations falling below a maximum iteration value and/or an elapsed time falling below a maximum time limit. For example, software programs 144 can keep a running count of the total number of iterations performed in which at each iteration the update to the structural estimate is performed, such as in accordance with Equation 2. The software programs 144 can also start a timer when the first update is performed. If the total number of iterations is less than a maximum iteration value, then the software programs 144 can perform the update to the structural estimate; and if otherwise, then the update is not performed. As another example, if the total time since the first update was performed is less than the maximum time limit, then the software programs 144 can perform the update to the structural estimate; and if otherwise, then the update is not performed.

In some cases, instead of or in addition to conditioning the performance of the update on the sum of the differences or the loss function defined by Equation 3, the stopping criterion (e.g., the condition for not performing the update) can include input requesting termination and display of a result. For example, a user input can be received during the process of performing the iterative image reconstruction. The input may request display of the current structural estimate. In response, the software programs 144 stop performing the update and display the current structural estimate. User input can be received to resume the process of performing the iterative image reconstruction. In response, the software programs 144 perform the last generated update and continue performing additional updates until another stopping criterion is met or satisfied.

For example, the software programs 144 access an updated structural estimate of the region of interest. The software programs 144 generate a second simulated X-ray measurement based on the updated structural estimate of the region of interest, such as in accordance with Equation 1. The software programs 144 receive a second real X-ray measurement from the CBCT system. The software programs 144 generate a further update to the updated structural estimate of the region of interest as a function of the second simulated X-ray measurement and the second real X-ray measurement, such as in accordance with Equation 2.

In some examples, the software programs 144 reduce a number of iterations and efficiency of generating the updates to the structural estimate by portioning the X-ray measurements into measurement groups and only performing an update if a given real X-ray measurement falls into a group associated with updating the structural estimate. Specifically, the software programs 144 receive a plurality of real X-ray measurements. The X-ray measurements are partitioned into measurement groups, in which a first measurement group of the measurement groups corresponds to a group of X-ray measurements used to update the current X-ray attenuation map, and a second measurement group of the measurement groups corresponds to a group of X-ray measurements that is skipped from updating the current X-ray structural estimate. The software programs 144 determines that the first real X-ray measurement falls within the first measurement group and, in response, the software programs 144 perform the update to the current structural estimate.

In some cases, the measurement groups are divided by number or quantity of real X-ray measurements that are received. For example, a queue may be maintained in which the real X-ray measurements are input. The queue may include a number of entries. As each new real X-ray measurement is received, the X-ray measurement is input to the queue. When the number of entries in the queue reaches a specified threshold, the last received X-ray measurement or a subset of last received X-ray measurements are used to perform an update to the structural estimate, such as in accordance with Equation 2. For example, when the number of entries in the queue reaches the specified threshold, the software programs 144 use Equation 1 to generate a simulated set of X-ray measurements which are used in combination with the last received X-ray measurement or a subset of last received X-ray measurements to generate the update to the current structural estimate. After the current structural estimate is updated, the queue is flushed and the entries are deleted so that 0 entries remain in the queue. In this way, the next update is performed when the next set of real X-ray measurements fill up the entries in the queue to reach the specified threshold.

In some implementations, the current structural estimate is smoothed based on a collection of updates to the structural estimate. Specifically, the software programs 144 can add each computed new updated of the structural estimate to a collection of updates performed on the structural estimate. Each update in the collection corresponds to or is associated with a respective iteration of performing updates to the structural estimate. The software programs 144 can identify a pattern in the collected plurality of updates. The software programs 144 can adjust or perform a new update to the structural estimate based on the identified pattern in the collected plurality of updates. For example, the software programs 144 can generate a plurality of updates based on a plurality of previously generated simulated X-ray measurements and corresponding real X-ray measurements. Each of these updates is input to a collection and a machine learning model or heuristic is applied to the collection to identify a particular pattern. The software programs 144 can then generate a new simulated X-ray measurement and receive a new real X-ray measurement. The software programs 144 can compute a new update to the structural estimate based on the new simulated X-ray measurement and new real X-ray measurement, according to Equation 2. The software programs 144 can adjust the computed new update based on the particular pattern that has been identified in the collection of previous updates. This can smooth the updates by preventing performance of updates that are too large in a particular portion of the structural estimate.

In addition to the memory device 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer-executable instructions stored thereon. The processor 114 may send or receive medical images 146 to memory device 116. For example, the processor 114 may receive medical images 146 from the image acquisition device 132 via the communication interface 118 and network 120 to be stored in memory device 116. The processor 114 may also send medical images 146 stored in memory device 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., DVH information); or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a machine learning model, such as a neural network model, or generate intermediate 2D or 3D images, which may then subsequently be stored in memory device 116. The processor 114 may subsequently transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image: such software programs 144 when executed may train a boundary detector or utilize a shape dictionary.

The processor 114 may be a processing device, including one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application-specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce-, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory device 116, to perform various operations, processes, methods that will be explained in greater detail below.

The memory device 116 can store medical images 146. In some embodiments, the medical images 146 may include one or more MRI images (e.g., 2D MRI, 3D MRI, 2D streaming MRI, four-dimensional (4D) MRI, 4D volumetric MRI, 4D cine MRI, etc.), functional MRI images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis. PET images, X-ray images, fluoroscopic images, radiotherapy portal images. SPECT images, computer generated synthetic images (e.g., pseudo-CT images), aperture images, graphical aperture image representations of MLC leaf positions at different gantry angles, and the like. Further, the medical images 146 may also include medical image data, for instance, training images, ground truth images, contoured images, and dose images. In an embodiment, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the image processing device 112 may use to perform operations consistent with the disclosed embodiments.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DV D or other optical storage, a cassette tape, other magnetic storage device, or any other non-transitory medium that may be used to store information including image, data, or computer-executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory device 116 may store one or more software applications. Software applications stored in the memory device 116 may include, for example, an operating system 143 for common computer systems as well as for software-controlled devices. Further, the memory device 116 may store an entire software application, or only a part of a software application, that is executable by the processor 114. For example, the memory device 116 may store one or more radiation therapy treatment plans 142.

The image processing device 112 can communicate with the network 120 via the communication interface 118, which can be communicatively coupled to the processor 114 and the memory device 116. The communication interface 118 may provide communication connections between the image processing device 112 and radiotherapy system 100 components (e.g., permitting the exchange of data with external devices). For instance, the communication interface 118 may, in some embodiments, have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber. USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more systems in network 120 may form a distributed computing/simulation environment that collaboratively performs the embodiments described herein. In some embodiments, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory device 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed. MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown) While the processor-readable storage medium in an embodiment may be a single medium, the term "processor-readable storage medium" should be taken to include a single medium or multiple media (e.g., a centralized or distributed database, and/or associated caches and servers) that store the one or more sets of computer-executable instructions or data. The term "processor-readable storage medium" shall also be taken to include any medium that is capable of storing or encoding a set of instructions for execution by a processor and that cause the processor to perform any one or more of the methodologies of the present disclosure. The term "processor-readable storage medium" shall accordingly be taken to include, but not be limited to, solid-state memories and optical and magnetic media. For example, the processor-readable storage medium can be one or more volatile, non-transitory, or non-volatile tangible computer-readable media.

Image processor 114 may communicate with database 124 to read images into memory device 116 or store images from memory device 116 to database 124. For example, the database 124 may be configured to store a plurality of images (e.g., 3D MRI, 4D MRI, 2D MRI slice images. CT images, 2D Fluoroscopy images, X-ray images, raw data from MRI scans or CT scans, Digital Imaging and Communications in Medicine (DIMCOM) data, projection images, graphical aperture images, etc.) that the database 124 received from image acquisition device 132. Database 124 may store data to be used by the image processor 114 when executing software program 144 or when creating radiation therapy treatment plans 142. Database 124 may store the data produced by the trained machine learning mode, such as a neural network including the network parameters constituting the model learned by the network and the resulting estimated data. As referred to herein, "estimate" or "estimated" can be used interchangeably with "predict" or "predicted" and should be understood to have the same meaning. The image processing device 112 may receive the imaging data, such as a medical image 146 (e.g., 2D MRI slice images, CT images, 2D Fluoroscopy images, X-ray images, 3D MRI images, 4D MRI images, projection images, graphical aperture images, image contours, etc.) from the database 124, the radiation therapy device 130 (e.g., an MR-linac), and/or the image acquisition device 132 to generate a treatment plan 142.

In an embodiment, the radiotherapy system 100 can include an image acquisition device 132 that can acquire medical images (e.g., MRI images, 3D MRI, 2D streaming MRI, 4D volumetric MRI. CT images, cone-Beam CT, PET images, functional MRI images (e.g., fMRI. DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data By way of example, the images acquired by the image acquisition device 132 can be also stored by the image processing device 112 as medical images 146 in memory device 116.

In an embodiment, for example, the image acquisition device 132 may be integrated with the radiation therapy device 130 as a single apparatus (e.g., an MR-linac). Such an MR-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, the number of radiation beams to be used during therapy, the dose per beam, and the like.

The image processor 114 may generate the radiation therapy treatment plan 142 by using software programs 144 such as treatment planning software (such as Monaco®, manufactured by Elekta AB of Stockholm, Sweden). In order to generate the radiation therapy treatment plans 142, the image processor 114 may communicate with the image acquisition device 132 (e.g., a CT device, an MRI device, a PET device, an X-ray device, an ultrasound device, etc.) to access images of the patient and to delineate a target, such as a tumor, to generate contours of the images. In some embodiments, the delineation of one or more OARs, such as healthy tissue surrounding the tumor or in close proximity to the tumor, may be required. Therefore, segmentation of the OAR may be performed when the OAR is close to the target tumor In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MRI images. CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained and used to generate a contour of the image. Contours of the image can include data overlaid on top of the image that delineates one or more structures of the anatomy. In some cases, the contours can be files associated with respective images that specify the coordinates or 2D or 3D locations of various structures of the anatomy depicted in the images.

In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm. Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor: defining that the spinal cord, brain stem, and optic structures receive ≤45 Gy, ≤55 Gy and <54 Gy, respectively). The result of inverse planning may constitute a radiation therapy treatment plan 142 that may be stored in memory device 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may use to input information to radiotherapy system 100. Alternatively, the display device 134 and the user interface 136 may be integrated into a device such as a tablet computer (e.g., Apple iPad®, Lenovo Thinkpad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, and the image acquisition device 132 could be implemented as a virtual machine. Given the processing power, memory, and computational capability available, the entire radiotherapy system 100 could be implemented as a virtual machine.

Figure 2A:
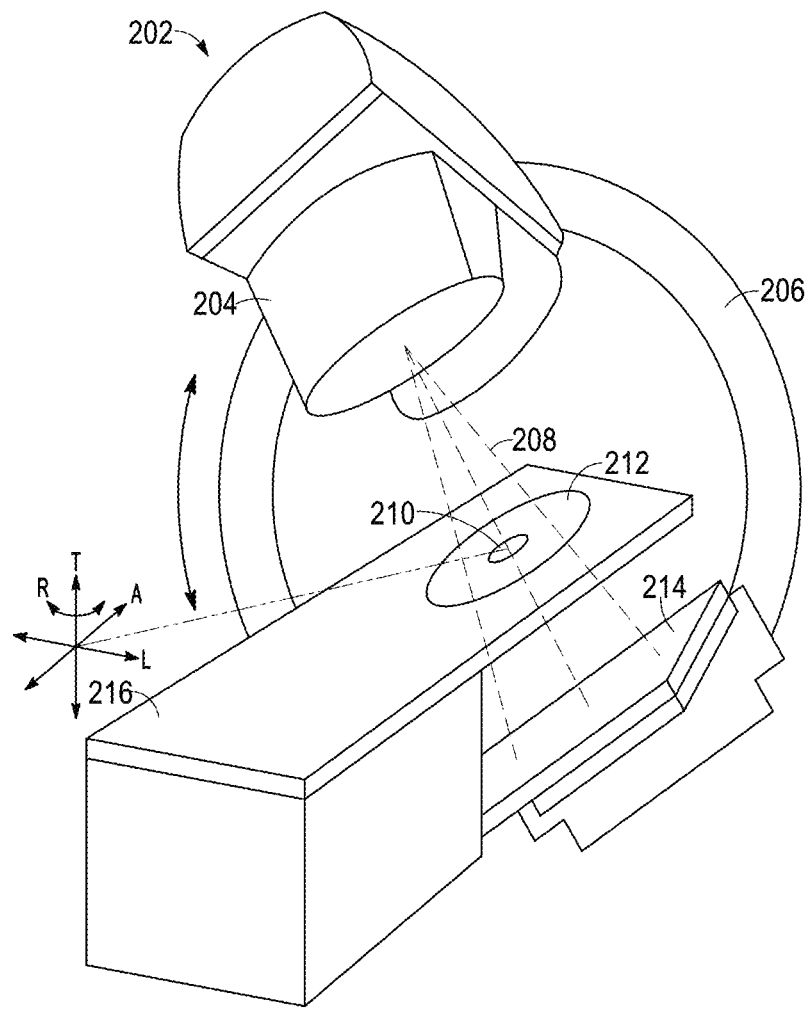
FIG. 2A illustrates an example radiation therapy system that can include radiation therapy output configured to provide a therapy beam, according to some embodiments of the present disclosure.

FIG. 2A illustrates an example radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC as described in the illustrative embodiment of FIG. 5, below.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch's 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can precisely target the tumor. The MLC may be integrated and included within gantry 206 to deliver the radiation beam 208 of a certain shape.

The coordinate system (including axes A, T. and L) shown in FIG. 2A can have an origin located at an isocenter 210. The isocenter 210 can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an embodiment, the imaging detector 214 can be located within a field of the therapy beam 208.

The imaging detector 214 can be mounted on the gantry 206 (preferably opposite the radiation therapy output 204), such as to maintain alignment with the therapy beam 208. The imaging detector 214 rotates about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging (e.g., to provide real X-ray measurements). The control circuitry of radiation therapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue near the therapy locus can be reduced or avoided.

Figure 2B:
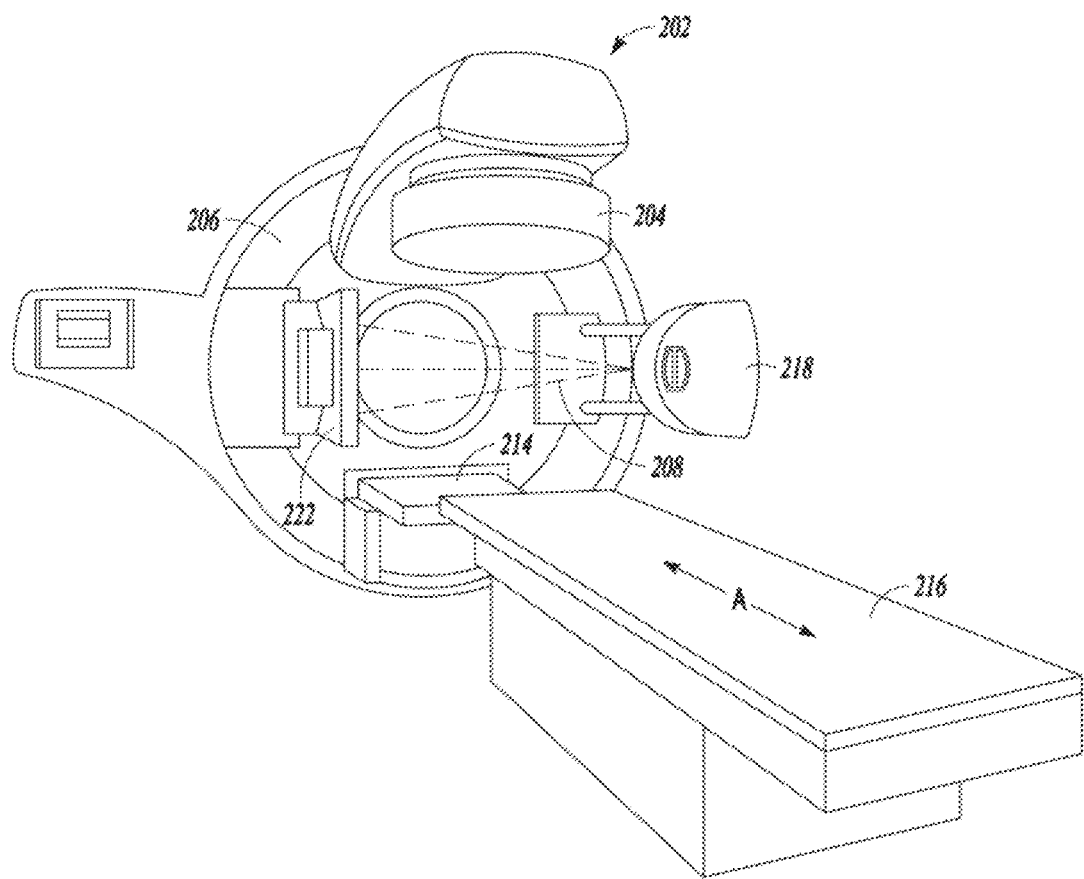
FIG. 2B illustrates an example system including a combined radiation therapy system and an imaging system, such as a cone beam computed tomography (CBCT) imaging system, according to some embodiments of the present disclosure.

FIG. 2B illustrates an example radiation therapy device 202 that may include a combined linac and an imaging system, such as can include a CT imaging system. The radiation therapy device 202 can include an MLC (not shown). The CT imaging system can include an imaging X-ray source 218, such as providing X-ray energy in a kiloelectron-Volt (keV) energy range which can be used for imaging the patient's anatomy, such as portal imaging (e.g., to provide real X-ray measurements). The imaging X-ray source 218 can provide a fan-shaped and/or a conical beam 208 directed to an imaging detector 222, such as a flat panel detector The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

In the illustrative embodiment of FIG. 213, the radiation therapy output 204 and the X-ray source 218 can be mounted on the same rotating gantry 206, rotationally-separated from each other by 9 degrees. In another embodiment, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
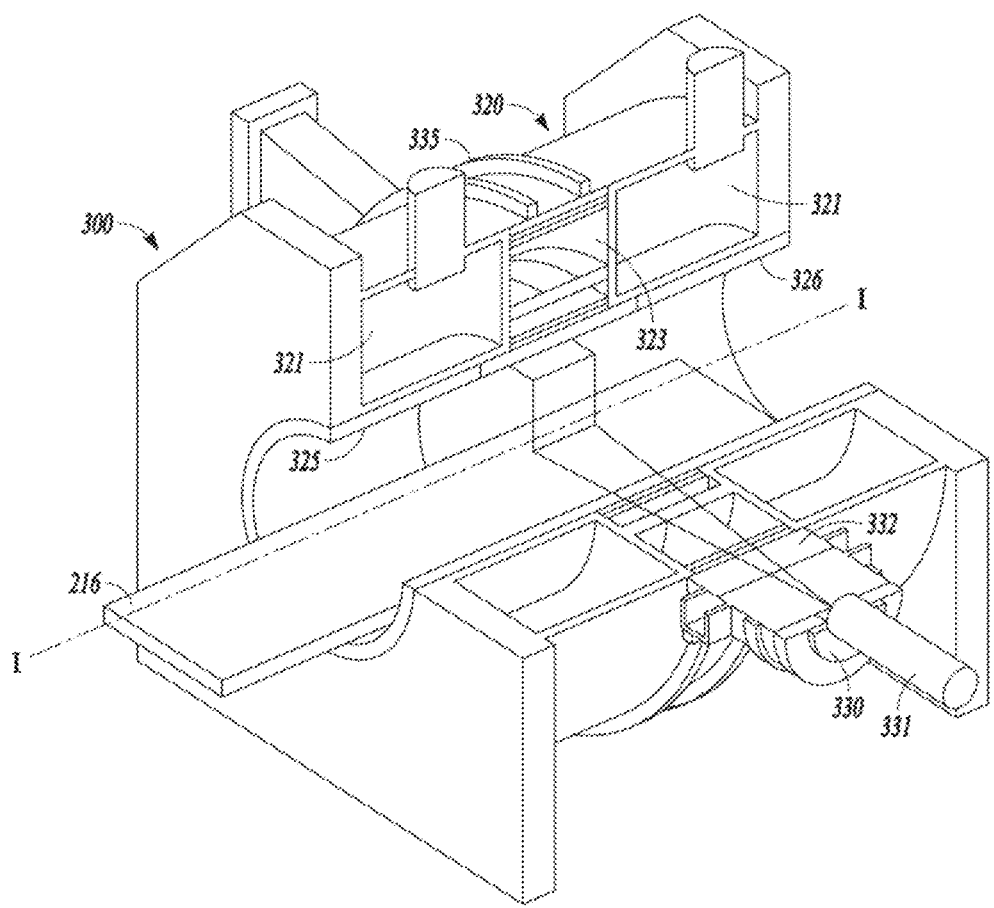
FIG. 3 illustrates a partially cut-away view of an example system including a combined radiation therapy system and an imaging system, such as a nuclear MR imaging (MRI) system, according to some embodiments of the present disclosure.
Figure 4A:
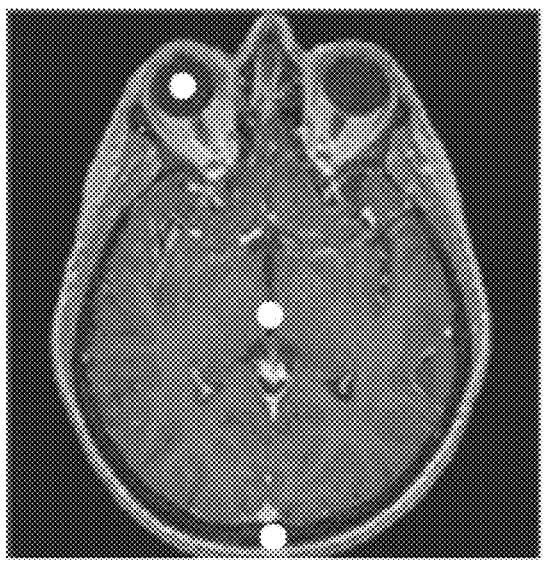
FIGS. 4A and 4B depict the differences between an example MRI image and a corresponding CT image, respectively, according to some embodiments of the present disclosure.
Figure 4B:
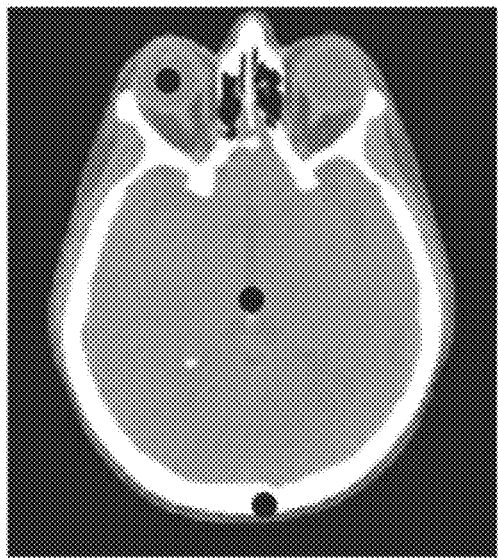

FIG. 3 depicts an example radiation therapy system 300 that can include combining a radiation therapy device 202 and an imaging system, such as a nuclear MR imaging system (e.g., known in the art as an MR-linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first modality (e.g., MRI image shown in FIG. 4A) or destination images of a second modality (e.g., CT image shown in FIG. 4B).

Couch 216 may support a patient (not shown) during a treatment session. In some implementations, couch 216 may move along a horizontal translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch 216 to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326 which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321 and may be displaced along that central axis. The displacement may create a gap, or window, between coils 325 and 326. In embodiments where magnet 321 can also include a central window 323 between coils, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

Radiotherapy device 330 may include the radiation source 331, such as an X-ray source or a linac, and an MLC 332 (shown below in FIG. 5) Radiotherapy device 330 may be mounted on a chassis 335. One or more chassis motors (not shown) may rotate chassis 335 around couch 216 when couch 216 is inserted into the treatment area. In an embodiment, chassis 335 may be continuously rotatable around couch 216 when couch 216 is inserted into the treatment area. Chassis 335 may also have an attached radiation detector (not shown), preferably located opposite to radiation source 331 and with the rotational axis of chassis 335 positioned between radiation source 331 and the detector Further, device 330 may include control circuitry (not shown) used to control, for example, one or more of couch 216, image acquisition device 320, and radiotherapy device 330. The control circuitry of radiotherapy device 330 may be integrated within system 300 or remote from it.

During a radiotherapy treatment session, a patient may be positioned on couch 216. System 300 may then move couch 216 into the treatment area defined by magnet 321, coils 325 and 326, and chassis 335. Control circuitry may then control radiation source 331. MLC 332, and the chassis motor(s) to deliver radiation to the patient through the window between coils 325 and 326 according to a radiotherapy treatment plan.

FIG. 2A. FIG. 2B, and FIG. 3 illustrate generally embodiments of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

Figure 5:
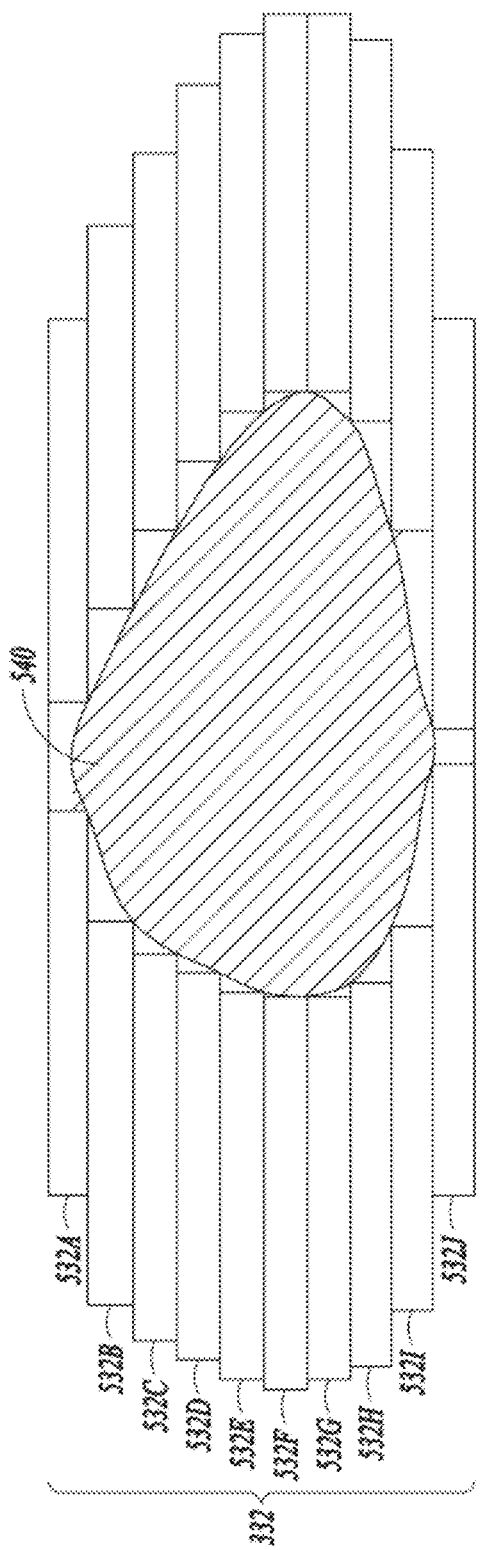
FIG. 5 illustrates an example collimator configuration for shaping, directing, or modulating an intensity of a radiation therapy beam, according to some embodiments of the present disclosure.

As discussed above, radiation therapy devices described by FIG. 2A, FIG. 2B, and FIG. 3 include an MLC for shaping, directing, or modulating an intensity of a radiation therapy beam to the specified target locus within the patient. FIG. 5 illustrates an example MLC 332 that includes leaves 532A through 532J that can be automatically positioned to define an aperture approximating a tumor 540 cross section or projection. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 532J can include metallic plates, such as comprising tungsten, with a long axis of the plates oriented parallel to a beam direction and having ends oriented orthogonally to the beam direction (as shown in the plane of the illustration of FIG. 2A) A "state"

of the MLC 332 can be adjusted adaptively during a course of radiation therapy treatment, such as to establish a therapy beam that better approximates a shape or location of the tumor 540 or another target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor can be referred to as IMRT.

Figure 6:
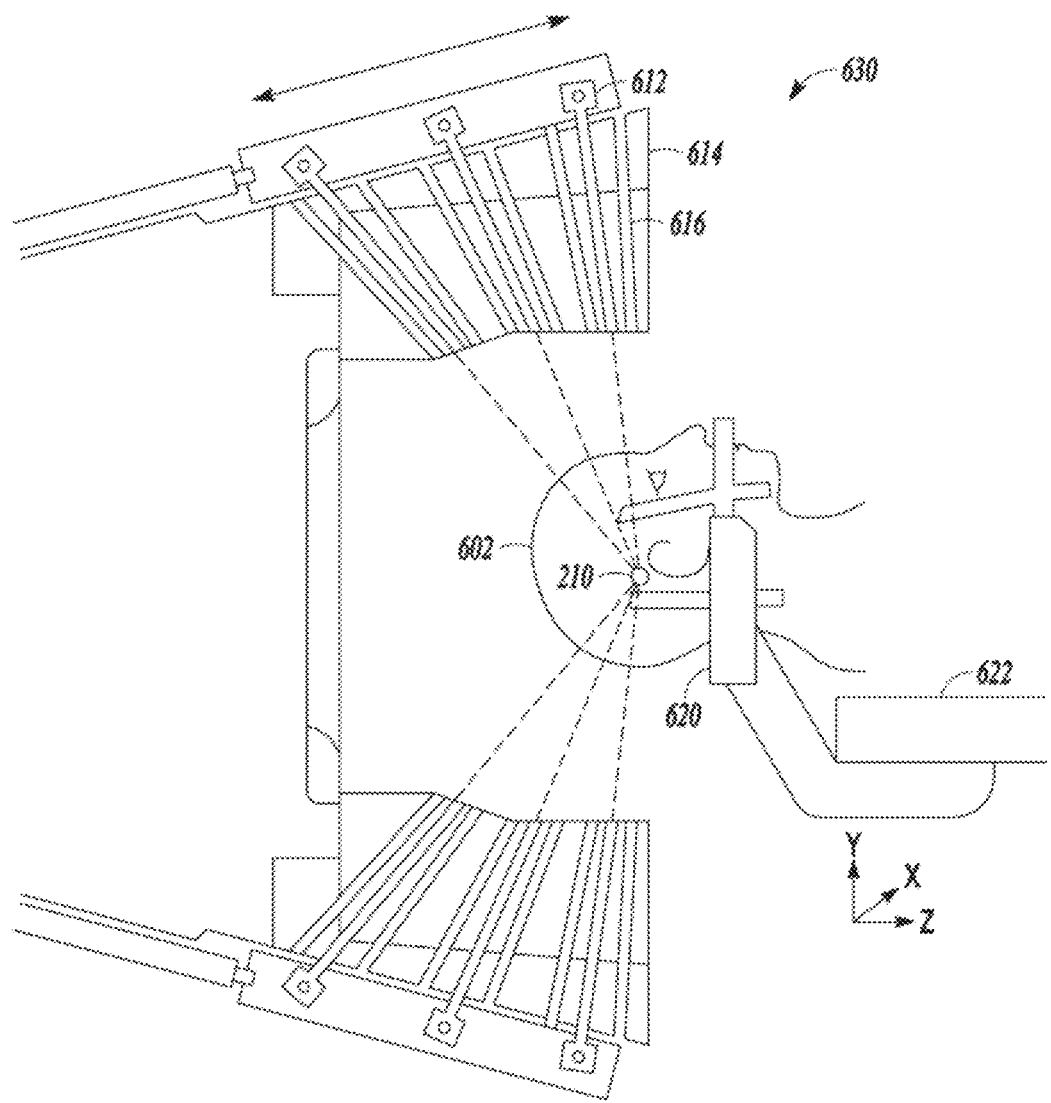
FIG. 6 illustrates an example Gamma Knife radiation therapy system, according to some embodiments of the present disclosure.

FIG. 6 illustrates an embodiment of another type of radiotherapy device 630 (e.g., a Leksell Gamma Knife), according to some embodiments of the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612. Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

Figure 7:
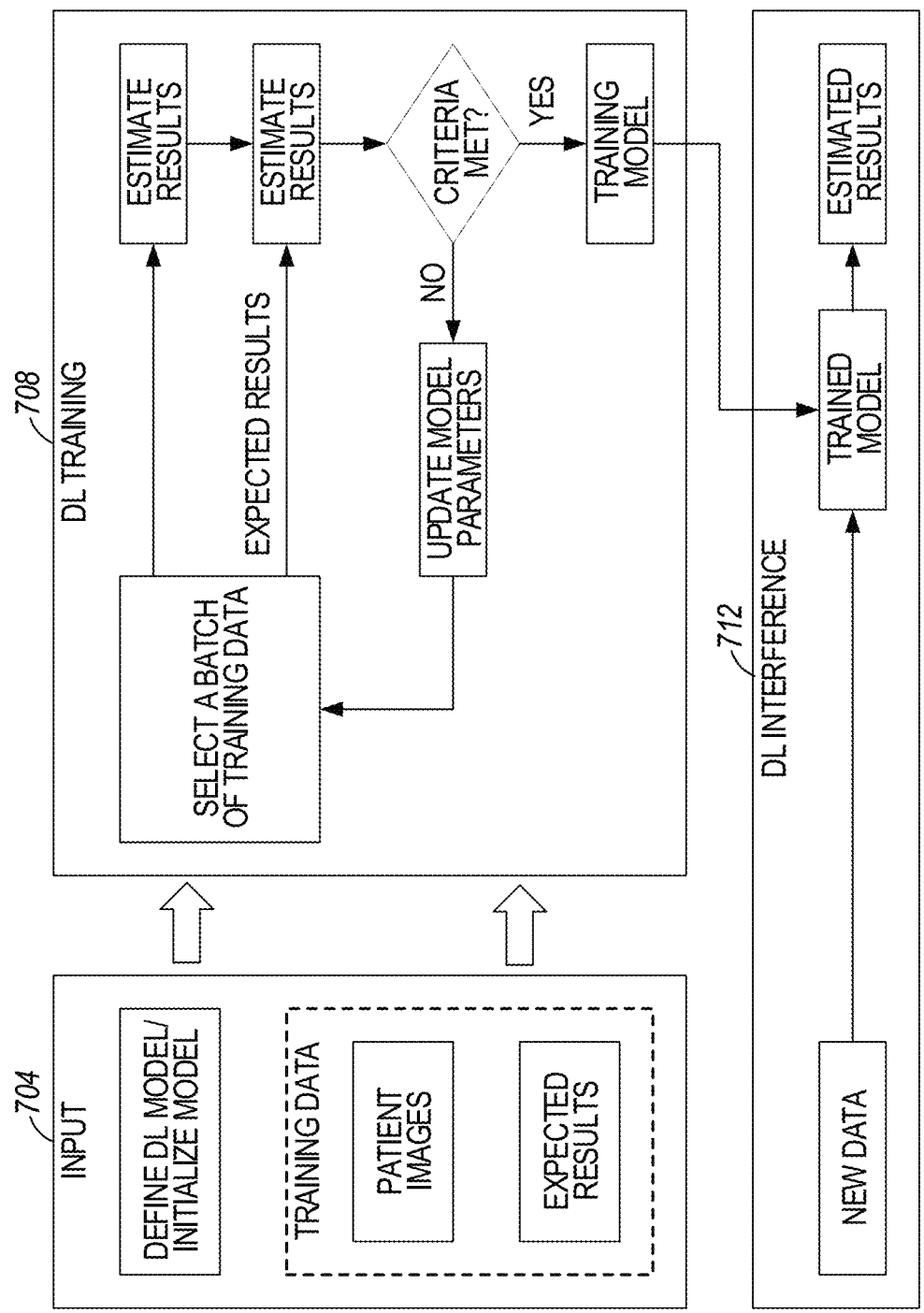
FIG. 7 illustrates an example flow diagram for deep learning, according to some embodiments of the present disclosure.

FIG. 7 illustrates an example flow diagram for deep learning, where a deep learning model (or a machine learning model), such as a deep convolutional neural network (DCNN), can be trained and used to determine a simulated X-ray measurement and/or an update to a structural model based on a simulated X-ray measurement and a real X-ray measurement. Namely, in one example, one or more DCNN models can be trained to establish a relationship between a training current structural model (e.g., an X-ray attenuation map) and a training known simulated X-ray measurement. In another example, one or more DCNN models can be trained to establish a relationship between a pair of training simulated X-ray measurement and real X-ray measurement and a training known update to a structural model (e.g., an X-ray attenuation map).

Inputs 704 can include a defined deep learning model (which can include one or more sub-networks or one or more individual and independent machine learning models) having an initial set of values and training data. The training data can include patient images, structural models, simulated X-ray measurements, real X-ray measurements, and expected results. The training data can also include paired data sets, such as a pair of a current structural model and a known simulated X-ray measurement. The training data can also include paired data sets, such as a pair of training simulated X-ray measurement and real X-ray measurement and a training known update to a structural model. The training data can include multiple of these paired data sets for multiple patients.

The deep learning model can include one or more neural networks (referred to as sub-networks), such as a DCNN. The deep learning network can be trained on the training data. For example, the deep learning network can be trained based on multiple batches of paired structural models and known simulated X-ray measurements. The deep learning network can be trained based on multiple batches of paired simulated X-ray measurement and real X-ray measurement and known updates to a structural model. In one embodiment, the deep learning network is trained in an end-to-end manner in which all of the sub-networks are trained simultaneously by being applied to a same set or batch of training data and minimizing a set of cost functions. In another embodiment, one or more of the sub-networks of the DCNN are trained separately and independently in sequence by minimizing a set of cost functions associated with each particular sub-network.

The training real X-ray measurements can include images of an anatomy or region of interest provided by one or more CT images, PET images, X-ray images, or MRI images across one or more treatment fractions. When trained, the deep learning network can produce a simulated X-ray measurement; and/or the deep learning network can produce an update to a structural model based on a simulated X-ray measurement and a real X-ray measurement. In one implementation, the expected results can include the known simulated X-ray measurement associated with a given structural model. In another implementation, the expected results can include the known update to the given structural model associated with a pair of simulated and real X-ray measurements.

During training of a first of the deep learning (DL) model 708, a batch of training data can be selected from the pairs of a training structural model and expected results (e.g., the corresponding ground-truth simulated X-ray measurement). In the case of end-to-end training, the batch of training data can be processed by all of the sub-networks of the DL model 708 simultaneously. In this case, a set of cost functions is minimized, the set of cost functions including a term based on a difference between an estimated simulated X-ray measurement produced by the first DL model 708 and the ground-truth simulated X-ray measurement of the training structural model. The set of cost functions may also be a combination of individual cost functions that act on various network outputs. In the case of individual and sequential training of the sub-networks, the same or a different set of training data may be used to train each sub-network.

The first deep learning model 708 can be applied to the selected training structural model to provide estimated results (e.g., estimated simulated X-ray measurements), which can then be compared to the expected results (e.g., ground truth simulated X-ray measurements associated with the training structural model) to compute a difference or deviation that can provide an indication of training errors. The errors can be used during a procedure called backpropagation to update the parameters of the first deep learning network (e.g., layer node weights and biases of each or of certain sub-networks of the model 708), in order to reduce or minimize errors during subsequent trials. The errors can be compared to predetermined criteria, such as proceeding to a sustained minimum for a specified number of training iterations. If the errors do not satisfy the predetermined criteria, then model parameters of the first deep learning model 708 can be updated using backpropagation, and another batch of training data can be selected from the other sets of training data (of the same patient or other patients) and expected results for another iteration of deep learning model training. If the errors satisfy the predetermined criteria, then the training can be ended, and the trained first model 708 can then be used during a deep learning testing or inference stage 712 to estimate simulated X-ray measurements based on structural models received during one or more treatment fractions. The trained first model 708 can receive a new current structural model and provide estimated results (e.g., the simulated X-ray measurements for the current structural model).

After updating the parameters of the DCNN, the iteration index can be incremented by a value of one. The iteration index can correspond to a number of times that the parameters of the DCNN have been updated. Stopping criteria can be computed, and if the stopping criteria are satisfied, then the DCNN model can be saved in a memory, such as the memory device 116 of image processing device 112, and the training can be halted if the stopping criteria are not satisfied, then the training can continue by obtaining another batch of training data from the same training subject or another training subject. In an embodiment, the stopping criteria can include a value of the iteration index (e.g., the stopping criteria can include whether the iteration index is greater than or equal to a determined maximum number of iterations). In an embodiment, the stopping criteria can include an accuracy of the output simulated X-ray measurement (e.g., the stopping criteria can include whether the difference between the output simulated X-ray measurement and the ground-truth simulated X-ray measurement in the batch of training data is smaller than a threshold).

After the first DL model 708 is trained, a current structural model of an anatomy can be received from an image acquisition device, such as image acquisition device 132. A trained DCNN model can be received from a network, such as the network 120, or from a memory, such as the memory device 116 of image processing device 112. The trained DCNN can be used to determine the estimated simulated X-ray measurement of the current structural model. This simulated X-ray measurement can be compared with the real X-ray measurement to generate an update to the current structural model, as discussed above and below.

During training of a second of the deep learning (DL) model 708, a batch of training data can be selected from the pairs of a training simulated X-ray measurement and real X-ray measurement and expected results (e.g., the corresponding ground-truth update to a structural model). In the case of end-to-end training, the batch of training data can be processed by all of the sub-networks of the DL model 708 simultaneously. In this case, a set of cost functions is minimized, the set of cost functions including a term based on a difference between an estimated update to the structural model produced by the second DL model 708 and the ground-truth update to the structural model. The set of cost functions may also be a combination of individual cost functions that act on various network outputs. In the case of individual and sequential training of the sub-networks, the same or different set of training data may be used to train each sub-network.

The second deep learning model 708 can be applied to the selected training simulated X-ray measurement and real X-ray measurement to provide estimated results (e.g., estimated update to the structural model), which can then be compared to the expected results (e.g., ground truth update to the structural model) to compute a difference or deviation that can provide an indication of training errors. The errors can be used during a procedure called backpropagation to update the parameters of the second deep learning network (e.g., layer node weights and biases of each or of certain sub-networks of the model 708), in order to reduce or minimize errors during subsequent trials. The errors can be compared to predetermined criteria, such as proceeding to a sustained minimum for a specified number of training iterations. If the errors do not satisfy the predetermined criteria, then model parameters of the second deep learning model 708 can be updated using backpropagation, and another batch of training data can be selected from the other sets of training data (of the same patient or other patients) and expected results for another iteration of deep learning model training. If the errors satisfy the predetermined criteria, then the training can be ended, and the trained second model 708 can then be used during a deep learning testing or inference stage 712 to estimate updates to a structural model based on simulated and real X-ray measurements received during one or more treatment fractions. The trained second model 708 can receive a new set of simulated and real X-ray measurements and provide estimated results (e.g., the estimated update to the current structural model based on the set of simulated and real X-ray measurements).

After updating the parameters of the DCNN, the iteration index can be incremented by a value of one. The iteration index can correspond to a number of times that the parameters of the DCNN have been updated. Stopping criteria can be computed, and if the stopping criteria are satisfied, then the DCNN model can be saved in a memory, such as the memory device 116 of image processing device 112, and the training can be halted. If the stopping criteria are not satisfied, then the training can continue by obtaining another batch of training data from the same training subject or another training subject. In an embodiment, the stopping criteria can include a value of the iteration index (e.g., the stopping criteria can include whether the iteration index is greater than or equal to a determined maximum number of iterations). In an embodiment, the stopping criteria can include an accuracy of the output estimated update to the structural model (e.g., the stopping criteria can include whether the difference between the estimated update to the structural model and the ground-truth update to the structural model in the batch of training data is smaller than a threshold).

After the second DL model 708 is trained, a current set of simulated and real X-ray measurements associated with an anatomy can be received from an image acquisition device, such as image acquisition device 132. In some cases, the simulated X-ray measurement can be received by the second DL model 708 from the first DL model 708 based on the current structural model. A trained DCNN model can be received from a network, such as the network 120, or from a memory, such as the memory device 116 of image processing device 112. The trained DCNN can be used to determine the estimated update to the current structural model based on the set of simulated and real X-ray measurements.

Specifically, in one example, a current structural model is accessed. The first DL model 708 is applied to the current structural model to estimate a simulated X-ray measurement based on the current structural model. The simulated X-ray measurement generated by the first DL model 708 and a real X-ray measurement can be applied to a second DL model 708. The second DL model 708 estimates an update to the current structural model based on the simulated X-ray measurement generated by the first DL model 708 and the real X-ray measurement that is received. The update generated by the second DL model 708 can then be used to modify or make changes to the current structural model.

Figure 8:
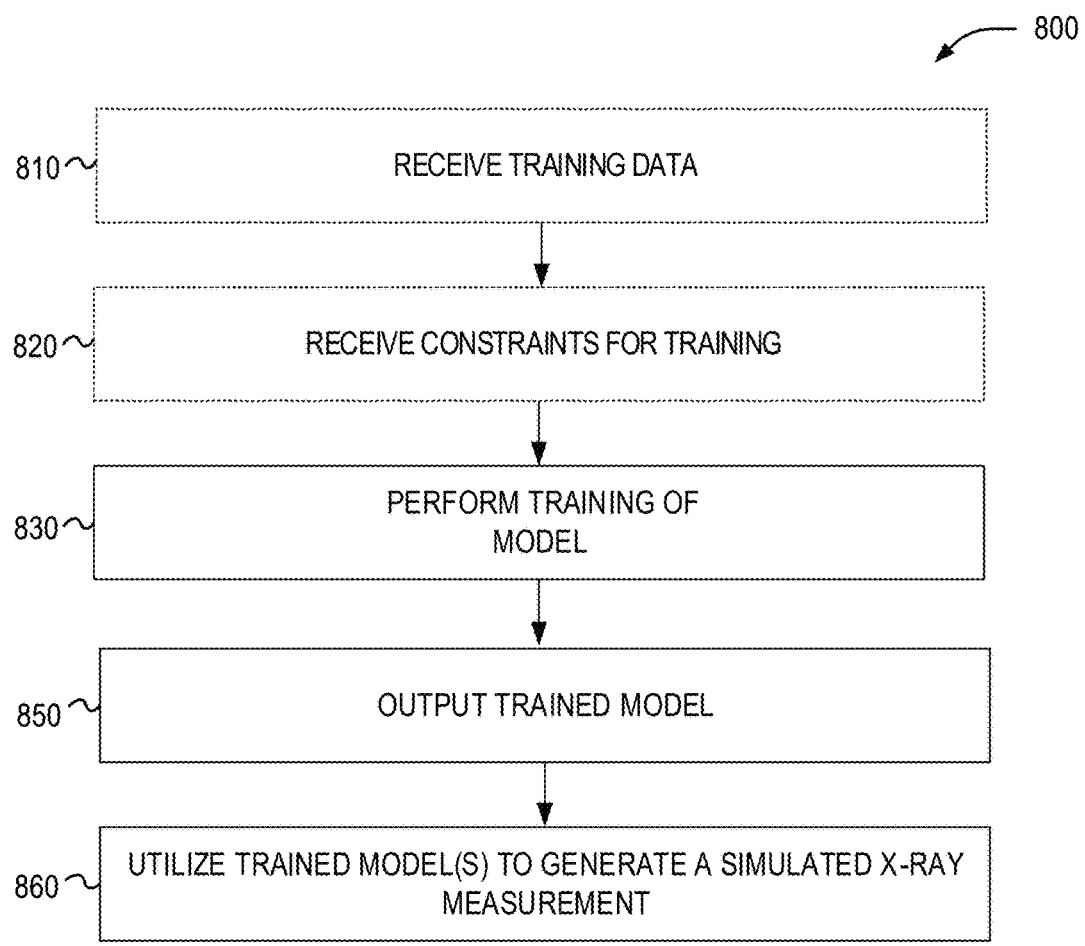
FIG. 8 illustrates an example data flow for training and use of a machine learning model to generate a simulated X-ray measurement or update to a structural estimate, according to some embodiments of the present disclosure.

FIG. 8 illustrates an example data flow of a process 800 for training and use of a machine learning model to generate a simulated X-ray measurement or update to a structural estimate, according to some embodiments of the present disclosure. The process 800 may be embodied in computer-readable instructions for execution by one or more processors such that the operations of the process 800 may be performed in part or in whole by the functional components of the image processing device 112; accordingly, the process 800 is described below by way of example with reference thereto. However, in other embodiments, at least some of the operations of the process 800 may be deployed on various other hardware configurations. The process 800 is therefore not intended to be limited to the image processing device 112 and can be implemented in whole, or in part, by any other component. Some or all of the operations of process 800 can be in parallel, out of order, or entirely omitted.

At operation 810, image processing device 112 receives training data. For example, image processing device 112 receives training data, which may include paired training data sets (e.g., input-output training pairs).

At operation 820, image processing device 112 receives one or more cost functions for training the model.

At operation 830, image processing device 112 performs training of the model based on the received training data and one or more cost functions.

At operation 850, image processing device 112 outputs the trained model. For example, image processing device 112 outputs the trained model to operate on a new set of X-ray measurements or a new structural estimate.

At operation 860, image processing device 112 utilizes the trained model to generate a simulated X-ray measurement or update to a structural estimate.

Figure 9:
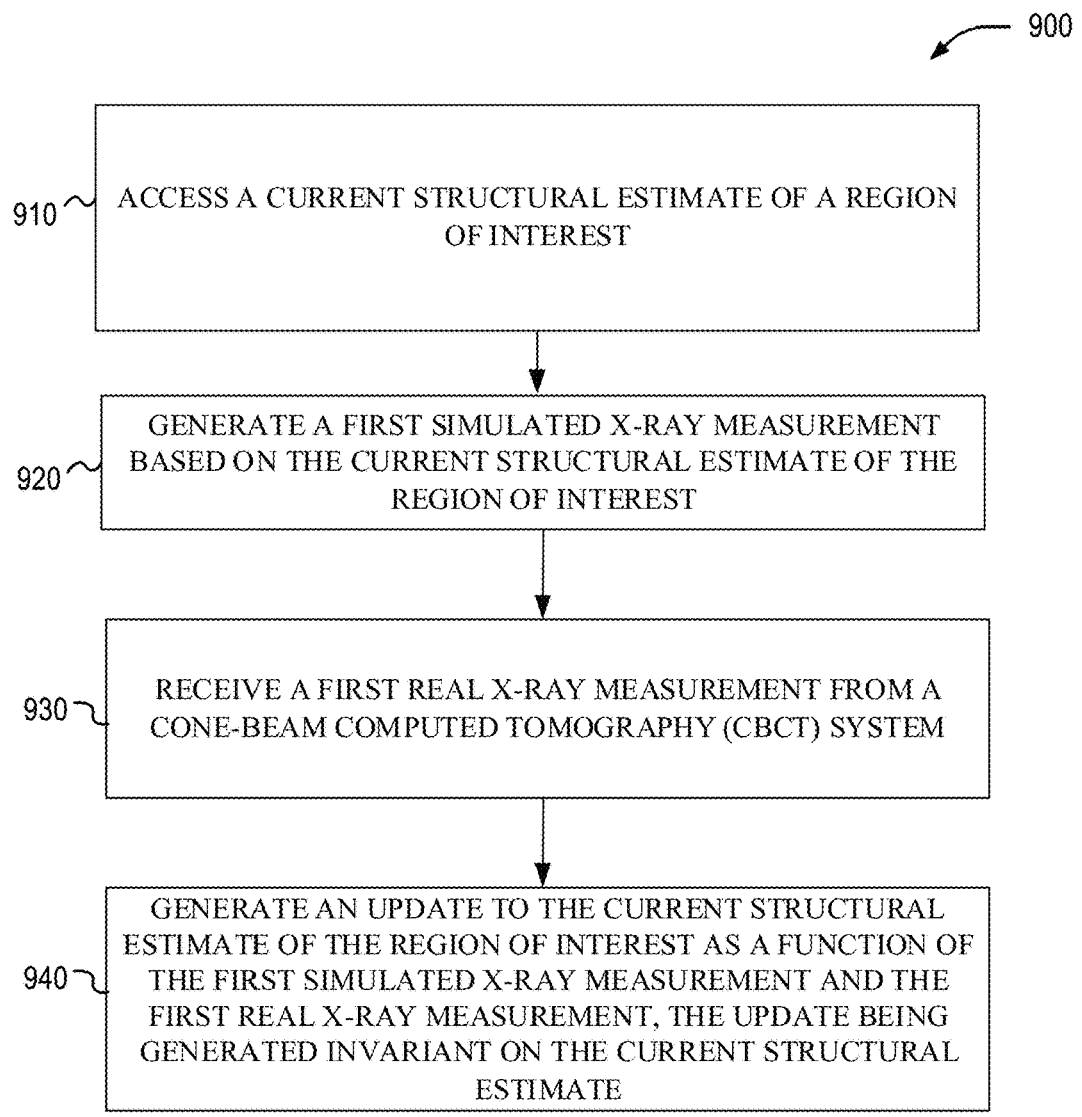
FIG. 9 illustrates a method for generating an update to a structural estimate of a region of interest, according to some embodiments of the present disclosure.

FIG. 9 illustrates a process 900 for generating an update to a structural estimate of a region of interest, according to some embodiments of the present disclosure. The process 900 may be embodied in computer-readable instructions for execution by one or more processors such that the operations of the process 900 may be performed in part or in whole by the functional components of the image processing device 112; accordingly, the process 900 is described below by way of example with reference thereto. However, in other embodiments, at least some of the operations of the process 900 may be deployed on various other hardware configurations. The process 900 is therefore not intended to be limited to the image processing device 12 and can be implemented in whole, or in part, by any other component. Some or all of the operations of process 900 can be in parallel, out of order, or entirely omitted.

At operation 910, image processing device 112 accesses a current structural estimate of a region of interest, as discussed above.

At operation 920, image processing device 112 generates a first simulated X-ray measurement based on the current structural estimate of the region of interest, as discussed above.

At operation 930, image processing device 112 receives a first real X-ray measurement from a CBCT system, as discussed above.

At operation 940, image processing device 112 generates an update to the current structural estimate of the region of interest as a function of the first simulated X-ray measurement and the first real X-ray measurement, the update being generated invariant on the current structural estimate, as discussed above.

Figure 10:
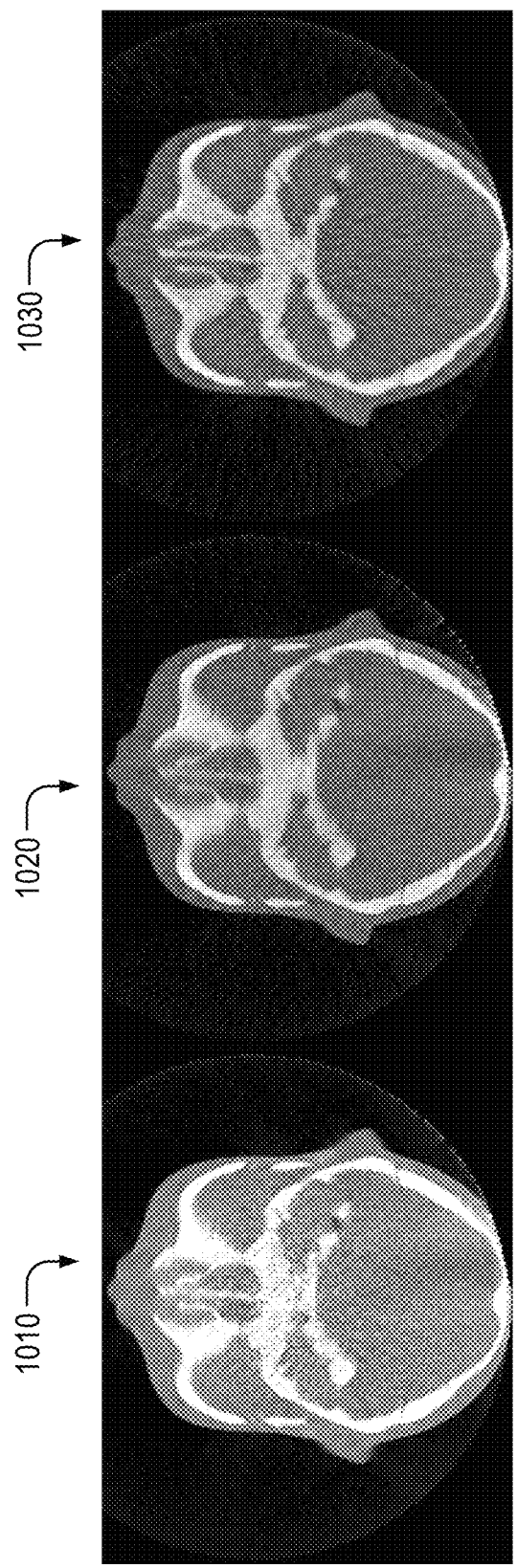
FIG. 10 depicts the differences between structural estimates generated according to different techniques, according to some embodiments of the present disclosure.

FIG. 10 depicts the differences between structural estimates generated according to different techniques, according to some embodiments of the present disclosure. Specifically, the images shown in FIG. 10 are iterative reconstructions of an anthropomorphic head phantom scanned on a cone-beam CT system. For example, a typical iteration reconstruction of an image is shown in image 1010. Image 1010 shows the result of iteration reconstruction (window [−985,1000] HU) of the anthropomorphic head phantom scanned on a cone-beam CT system based on minimizing a weighted-least squares (WLS) objective function after 50 iterations. Image 1020 shows the result of another typical iteration reconstruction based on minimizing the Poisson negative log-likelihood through monotone separable quadratic surrogates (SQS) for 150 iterations. Image 1030 shows a result of performing iterative reconstruction in accordance with the disclosed techniques after 50 iterations. As shown, the image 1030 resulting from the disclosed techniques includes less noise and phantoms than the images 1010 and 1020 resulting from the typical approaches. This demonstrates the speed and quality improvements of the disclosed approach over existing methods.

Figure 11:
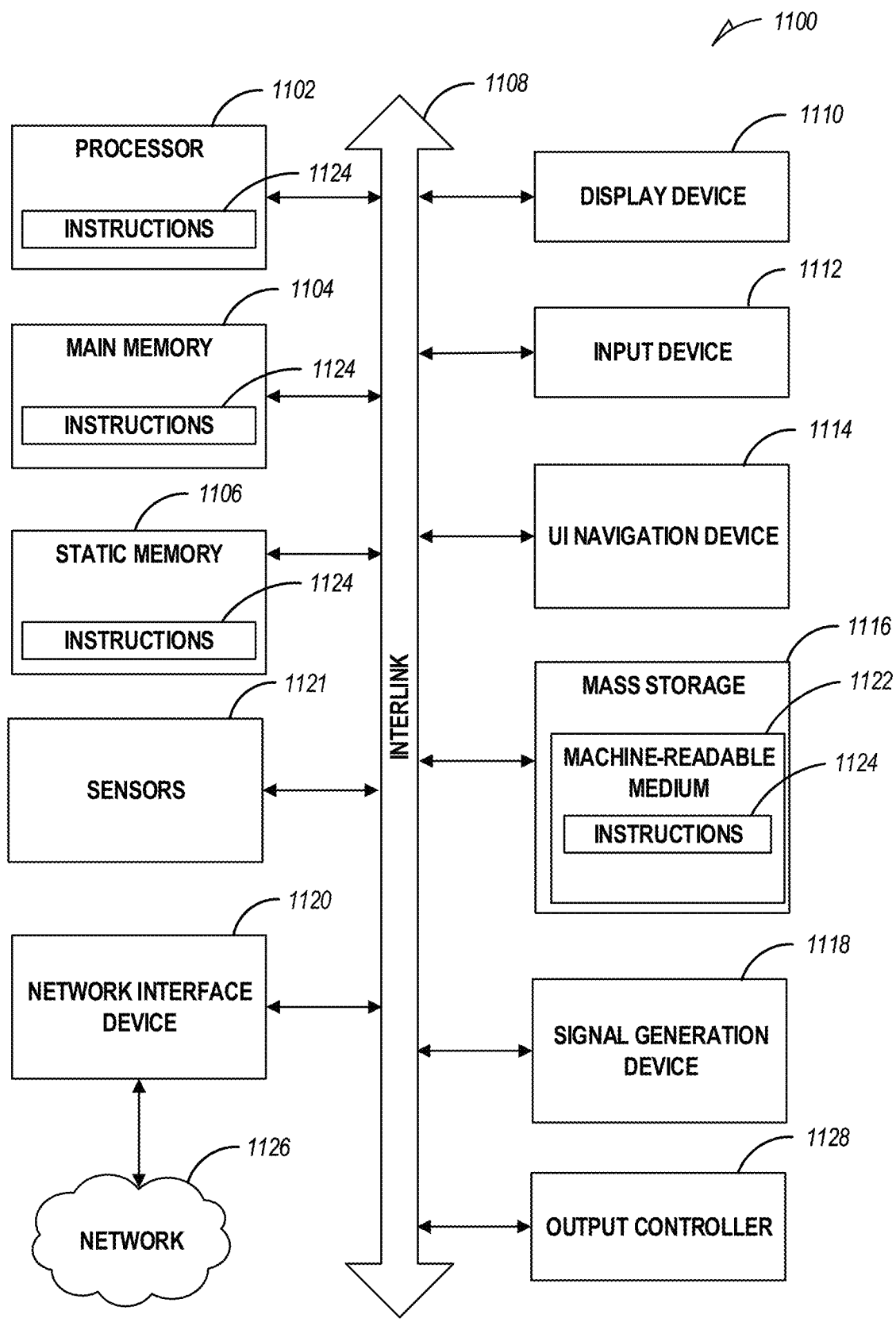
FIG. 11 illustrates an example block diagram of a machine on which one or more of the methods as discussed herein can be implemented.

FIG. 11 illustrates a block diagram of an embodiment of a machine 1100 on which one or more of the methods as discussed herein can be implemented. In one or more embodiments, one or more items of the image processing device 112 can be implemented by the machine 1100. In alternative embodiments, the machine 1100 operates as a standalone device or may be connected (e.g., networked) to other machines. In one or more embodiments, the image processing device 112 can include one or more of the items of the machine 1100. In a networked deployment, the machine 1100 may operate in the capacity of a server or a client machine in server-client network environment, or as a peer machine in a peer-to-peer (or distributed) network environment. The machine 1100 may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine 1100 is illustrated, the term "machine" shall also be taken to include any collection of machines that individually or jointly execute a set (or multiple sets) of instructions to perform any one or more of the methodologies discussed herein.

The example machine 1100 includes processing circuitry (e.g., the processor 1102, a CPU, a GPU, an ASIC, circuitry, such as one or more transistors, resistors, capacitors, inductors, diodes, logic gates, multiplexers, buffers, modulators, demodulators, radios (e.g., transmit or receive radios or transceivers), sensors 1121 (e.g., a transducer that converts one form of energy (e.g., light, heat, electrical, mechanical, or other energy) to another form of energy), or the like, or a combination thereof), a main memory 1104 and a static memory 1106, which communicate with each other via a bus 1108. The machine 1100 (e.g., computer system) may further include a video display unit 1110 (e.g., a liquid crystal display (LCD) or a cathode ray tube (CRT)). The machine 1100 also includes an alphanumeric input device 1112 (e.g., a keyboard), a user interface (UI) navigation device 1114 (e.g., a mouse), a disk drive or mass storage unit 1116, a signal generation device 1118 (e.g., a speaker), and a network interface device 1120.

The disk drive or mass storage unit 1116 includes a machine-readable medium 1122 on which is stored one or more sets of data structures and instructions (e.g., software) 1124 embodying or utilized by any one or more of the methodologies or functions described herein. The instructions 1124 may also reside, completely or at least partially, within the main memory 1104 and/or within the processor 1102 during execution thereof by the machine 1100, the main memory 1104 and the processor 1102 also constituting machine-readable media.

The machine 1100 as illustrated includes an output controller 1128. The output controller 1128 manages data flow to/from the machine 1100. The output controller 1128 is sometimes called a device controller, with software that directly interacts with the output controller 11128 being called a device driver.

While the machine-readable medium 1122 is shown in an embodiment to be a single medium, the term "machine-readable medium" may include a single medium or multiple media (e.g., a centralized or distributed database, and/or associated caches and servers) that store the one or more instructions 1124 or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM). EEPROM, and flash memory devices; magnetic disks such as internal hard disks and removable disks; magneto-optical disks, and CD-ROM and DVD-ROM disks.

The instructions 1124 may further be transmitted or received over a communications network 1126 using a transmission medium. The instructions 1124 may be transmitted using the network interface device 1120 and any one of a number of well-known transfer protocols (e.g., HTTP). Examples of communication networks include a LAN, a WAN, the Internet, mobile telephone networks. Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that elements after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., ROMs), EPROMS, EEPROMS, or any type of media suitable for storing electronic instructions, and the like. Such computer-readable storage medium coupled to a computer system bus may be accessible by the processor and other parts of the OIS.

In an embodiment, the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, Compute Unified Device Architecture (CUDA), C, C++, Java, Python, and the like; and using standard machine learning/deep learning library (or API), such as tensorflow, torch and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved, and other beneficial results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are example embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A system comprising:
  a memory; and
  one or more processors that, when executing instructions stored in the memory, are configured to perform operations comprising:
  accessing a current structural estimate of a region of interest; and
  using a trained machine learning model based on the current structural estimate of the region of interest to generate a first simulated X-ray measurement, the first simulated X-ray measurement being used with a first real X-ray measurement to generate an update for a structural estimate, the update generated invariant on the current structural estimate.

2. The system of claim 1, the operations comprising:
  receiving the first real X-ray measurement; and
  generating an update to the current structural estimate of the region of interest as a function of the first simulated X-ray measurement and the first real X-ray measurement.

3. The system of claim 1, wherein the operations further comprise:
   linearly projecting the update into an image space to form a perturbation;
   scaling the perturbation by a scalar for stability; and
   subtracting the scaled perturbation from a current structural estimate.

4. The system of claim 1, wherein the operations further comprise:
   applying at least one of regularization, momentum or denoising to the updated structural estimate.

5. The system of claim 1, wherein the current structural estimate comprises an X-ray attenuation map that represents a three-dimensional (3D) model of the region of interest.

6. The system of claim 5, wherein the X-ray attenuation map comprises a linear X-ray attenuation map.

7. The system of claim 1, wherein the machine learning model is trained to generate an expected output of a real X-ray measurement.

8. The system of claim 7, wherein the current structural estimate comprises an X-ray attenuation map, and wherein the machine learning model generates the expected output of the real X-ray measurement, for a given measurement index i per number of detector elements in a cone-beam computed tomography (CBCT) system, in accordance with:

$$z_i = b_i * \exp(-[Ax]_i) + r_i,$$

where b is an incident intensity of flood field, A is a system projection matrix describing a combination of each image pixel at each detector element, x is the current X-ray attenuation map, exp is an exponential function, and r is background noise including scatter.

9. The system of claim 8, wherein the operations further comprise re-estimating r representing the background noise including scatter based on the current structural estimate at each iteration of generating the update.

10. The system of claim 1, wherein the operations further comprise:
    accessing an updated structural estimate of the region of interest;
    generating a second simulated X-ray measurement based on the updated structural estimate of the region of interest;
    receiving a second real X-ray measurement; and
    generating a further update to the updated structural estimate of the region of interest as a function of the second simulated X-ray measurement and the second real X-ray measurement.

11. The system of claim 1, wherein the operations further comprise:
    accessing an objective function comprising a negative log-likelihood (NLL) function.

12. The system of claim 11, wherein the operations comprise:
    computing a loss by applying the NLL function to a combination of the first simulated X-ray measurement and a first real X-ray measurement.

13. The system of claim 12, wherein the operations comprise:
    in response to determining that the loss fails to satisfy a criterion, performing the update to the current structural estimate, the criterion comprising a difference between adjacent updates falling below a threshold, a number of iterations falling below a maximum iteration value, an elapsed time falling below a maximum time limit, or input requesting termination and display of a result.

14. The system of claim 1, wherein the current structural estimate comprises an X-ray attenuation map, and wherein the update to the current structural estimate of the region of interest is computed in accordance with:

$$A^T(y/(b*\exp(-Ax)+r)-1),$$

where A is a system projection matrix describing a combination of each image pixel at each detector element, $A^T$ is a transpose of the system projection matrix, y is a first real X-ray measurement, b is an incident intensity of flood field, x is the X-ray attenuation map, exp is an exponential function, and r is background noise including scatter.

15. The system of claim 1, wherein the operations further comprise:
    receiving a plurality of real X-ray measurements; and
    partitioning the plurality of real X-ray measurements into measurement groups, a first measurement group of the measurement groups corresponding to a group of X-ray measurements used to update the current structural estimate, and a second measurement group of the measurement groups corresponding to a group of X-ray measurements that is skipped from updating the current structural estimate.

16. The system of claim 15, wherein the operations comprise:
    determining that a first real-X-ray measurement falls within the first measurement group; and
    in response to determining that the first real-X-ray measurement falls within the first measurement group, performing the update to the current structural estimate.

17. The system of claim 1, wherein the operations further comprise:
    collecting a plurality of updates to the current structural estimate, each of the plurality of updates being associated with a respective iteration;
    identifying a pattern of updates based on the collected plurality of updates; and
    performing the update to the current structural estimate based on the identified pattern of updates.

18. A method comprising:
    accessing, by one or more hardware processors, a current structural estimate of a region of interest; and
    using a trained machine learning model based on the current structural estimate of the region of interest to generate a first simulated X-ray measurement, the first simulated X-ray measurement being used with a first real X-ray measurement to generate an update for a structural estimate, the update generated invariant on the current structural estimate.

19. The method of claim 18, further comprising:
    linearly projecting the update to the current structural estimate into an image space to form a perturbation;
    scaling the perturbation by a scalar for stability; and
    subtracting the scaled perturbation from the current structural estimate to generate an updated structural estimate.

20. A non-transitory computer-readable medium comprising non-transitory computer-readable instructions that, when executed by one or more processors, configure the one or more processors to perform operations comprising:

accessing a current structural estimate of a region of interest; and using a trained machine learning model based on the current structural estimate of the region of interest to generate a first simulated X-ray measurement, the first simulated X-ray measurement being used with a first real X-ray measurement to generate an update for a structural estimate, the update generated invariant on the current structural estimate.

* * * * *